US012685633B2

(12) United States Patent
Buesseler et al.

(10) Patent No.: US 12,685,633 B2
(45) Date of Patent: Jul. 21, 2026

(54) BOWED RUNNERS FOR PARAVALVULAR LEAK PROTECTION

(71) Applicant: St. Jude Medical, Cardiology Division, Inc., St. Paul, MN (US)

(72) Inventors: Ryan Buesseler, Delano, MN (US); Ott Khouengboua, Chaska, MN (US); Jane M. Korfe, Buffalo, MN (US); Kristopher Henry Vietmeier, Monticello, MN (US); Saravana B. Kumar, Minnetonka, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 603 days.

(21) Appl. No.: 18/301,549

(22) Filed: Apr. 17, 2023

(65) Prior Publication Data

US 2023/0270542 A1 Aug. 31, 2023

Related U.S. Application Data

(62) Division of application No. 15/119,566, filed as application No. PCT/US2015/015537 on Feb. 12, 2015, now Pat. No. 11,672,652.

(Continued)

(51) Int. Cl.
*A61F 2/24* (2006.01)

(52) U.S. Cl.
CPC .......... *A61F 2/2418* (2013.01); *A61F 2/2412* (2013.01); *A61F 2230/0078* (2013.01);
(Continued)

(58) Field of Classification Search
CPC .................. A61F 2/2418; A61F 2/2412; A61F 2230/0054; A61F 2220/0016;
(Continued)

(56) References Cited

U.S. PATENT DOCUMENTS

| | | | |
|---|---|---|---|
| 4,275,469 A | 6/1981 | Gabbay |
| 4,491,986 A | 1/1985 | Gabbay |

(Continued)

FOREIGN PATENT DOCUMENTS

| | | |
|---|---|---|
| DE | 19857887 B4 | 5/2005 |
| DE | 10121210 B4 | 11/2005 |

(Continued)

OTHER PUBLICATIONS

"Transluminal Implantation of Artificial Heart Valves", Andersen, H. R., et al., European Heart Journal, vol. 13, No. 5, May 1992, pp. 704-708.

(Continued)

*Primary Examiner* — Katherine M Shi
(74) *Attorney, Agent, or Firm* — SLEMAN & LUND LLP

(57) ABSTRACT

A prosthetic heart valve for replacing a native valve includes a collapsible and expandable stent having a proximal end and a distal end, the stent being formed of a plurality of struts forming cells. A valve assembly is disposed within the stent, the valve assembly including a plurality of leaflets and a cuff. At least one runner is coupled to a cell and configured to transition from a first configuration to a second configuration when the stent moves from the collapsed condition to the expanded condition.

11 Claims, 10 Drawing Sheets

Related U.S. Application Data

(60) Provisional application No. 61/941,024, filed on Feb. 18, 2014.

(52) U.S. Cl.
CPC ................. *A61F 2250/0039* (2013.01); *A61F 2250/0069* (2013.01)

(58) Field of Classification Search
CPC ........... A61F 2/2436; A61F 2230/0078; A61F 2250/0039; A61F 2250/0069
See application file for complete search history.

(56) References Cited

U.S. PATENT DOCUMENTS

| | | | |
|---|---|---|---|
| 4,759,758 A | 7/1988 | Gabbay |
| 4,878,906 A | 11/1989 | Lindemann |
| 4,922,905 A | 5/1990 | Strecker |
| 4,994,077 A | 2/1991 | Dobben |
| 5,411,552 A | 5/1995 | Andersen |
| 5,480,423 A | 1/1996 | Ravenscroft |
| 5,855,601 A | 1/1999 | Bessler |
| 5,935,163 A | 8/1999 | Gabbay |
| 5,961,549 A | 10/1999 | Nguyen |
| 6,045,576 A | 4/2000 | Starr |
| 6,083,257 A | 7/2000 | Taylor |
| 6,090,140 A | 7/2000 | Gabbay |
| 6,214,036 B1 | 4/2001 | Letendre |
| 6,264,691 B1 | 7/2001 | Gabbay |
| 6,267,783 B1 | 7/2001 | Letendre |
| 6,368,348 B1 | 4/2002 | Gabbay |
| 6,419,695 B1 | 7/2002 | Gabbay |
| 6,458,153 B1 | 10/2002 | Bailey |
| 6,468,660 B2 | 10/2002 | Ogle |
| 6,488,702 B1 | 12/2002 | Besselink |
| 6,517,576 B2 | 2/2003 | Gabbay |
| 6,533,810 B2 | 3/2003 | Hankh |
| 6,582,464 B2 | 6/2003 | Gabbay |
| 6,610,088 B1 | 8/2003 | Gabbay |
| 6,652,578 B2 | 11/2003 | Bailey |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser |
| 6,783,556 B1 | 8/2004 | Gabbay |
| 6,790,230 B2 | 9/2004 | Beyersdorf |
| 6,869,444 B2 | 3/2005 | Gabbay |
| 6,893,460 B2 | 5/2005 | Spenser |
| 6,908,481 B2 | 6/2005 | Cribier |
| 6,951,573 B1 | 10/2005 | Dilling |
| 7,018,406 B2 | 3/2006 | Seguin |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz |
| 7,247,167 B2 | 7/2007 | Gabbay |
| 7,267,686 B2 | 9/2007 | DiMatteo |
| 7,276,078 B2 | 10/2007 | Spenser |
| 7,320,704 B2 | 1/2008 | Lashinski |
| 7,329,278 B2 | 2/2008 | Seguin |
| 7,374,573 B2 | 5/2008 | Gabbay |
| 7,381,218 B2 | 6/2008 | Schreck |
| 7,381,219 B2 | 6/2008 | Salahieh |
| 7,452,371 B2 | 11/2008 | Pavcnik |
| 7,510,575 B2 | 3/2009 | Spenser |
| 7,524,331 B2 | 4/2009 | Birdsall |
| 7,534,261 B2 | 5/2009 | Friedman |
| RE40,816 E | 6/2009 | Taylor |
| 7,585,321 B2 | 9/2009 | Cribier |
| 7,628,805 B2 | 12/2009 | Spenser |
| 7,708,775 B2 | 5/2010 | Rowe |
| 7,731,742 B2 | 6/2010 | Schlick |
| 7,748,389 B2 | 7/2010 | Salahieh |
| 7,780,725 B2 | 8/2010 | Haug |
| 7,799,069 B2 | 9/2010 | Bailey |
| 7,824,442 B2 | 11/2010 | Salahieh |
| 7,837,727 B2 | 11/2010 | Goetz |
| 7,846,203 B2 | 12/2010 | Cribier |
| 7,846,204 B2 | 12/2010 | Letac |
| 7,857,845 B2 | 12/2010 | Stacchino |
| 7,892,281 B2 | 2/2011 | Seguin |
| 7,914,569 B2 | 3/2011 | Nguyen |
| 7,959,666 B2 | 6/2011 | Salahieh |
| 7,959,672 B2 | 6/2011 | Salahieh |
| 7,972,378 B2 | 7/2011 | Tabor |
| 7,988,724 B2 | 8/2011 | Salahieh |
| 7,993,394 B2 | 8/2011 | Hariton |
| 8,016,877 B2 | 9/2011 | Seguin |
| D648,854 S | 11/2011 | Braido |
| 8,048,153 B2 | 11/2011 | Salahieh |
| 8,052,741 B2 | 11/2011 | Bruszewski |
| 8,052,749 B2 | 11/2011 | Salahieh |
| 8,052,750 B2 | 11/2011 | Tuval |
| 8,062,355 B2 | 11/2011 | Figulla |
| 8,075,611 B2 | 12/2011 | Millwee |
| D652,926 S | 1/2012 | Braido |
| D652,927 S | 1/2012 | Braido |
| D653,341 S | 1/2012 | Braido |
| D653,342 S | 1/2012 | Braido |
| D653,343 S | 1/2012 | Ness |
| D654,169 S | 2/2012 | Braido |
| D654,170 S | 2/2012 | Braido |
| 8,137,398 B2 | 3/2012 | Tuval |
| 8,142,497 B2 | 3/2012 | Friedman |
| D660,432 S | 5/2012 | Braido |
| D660,433 S | 5/2012 | Braido |
| D660,967 S | 5/2012 | Braido |
| 8,182,528 B2 | 5/2012 | Salahieh |
| 8,221,493 B2 | 7/2012 | Boyle |
| 8,230,717 B2 | 7/2012 | Matonick |
| 8,231,670 B2 | 7/2012 | Salahieh |
| 8,252,051 B2 | 8/2012 | Chau |
| 8,308,798 B2 | 11/2012 | Pintor |
| 8,313,525 B2 | 11/2012 | Tuval |
| 8,323,335 B2 | 12/2012 | Rowe |
| 8,323,336 B2 | 12/2012 | Hill |
| 8,343,213 B2 | 1/2013 | Salahieh |
| 8,348,995 B2 | 1/2013 | Tuval |
| 8,348,996 B2 | 1/2013 | Tuval |
| 8,348,998 B2 | 1/2013 | Pintor |
| 8,366,769 B2 | 2/2013 | Huynh |
| 8,403,983 B2 | 3/2013 | Quadri |
| 8,408,214 B2 | 4/2013 | Spenser |
| 8,414,643 B2 | 4/2013 | Tuval |
| 8,425,593 B2 | 4/2013 | Braido |
| 8,449,599 B2 | 5/2013 | Chau |
| 8,449,604 B2 | 5/2013 | Moaddeb |
| D684,692 S | 6/2013 | Braido |
| 8,454,686 B2 | 6/2013 | Alkhatib |
| 8,500,798 B2 | 8/2013 | Rowe |
| 8,568,474 B2 | 10/2013 | Yeung |
| 8,579,962 B2 | 11/2013 | Salahieh |
| 8,579,966 B2 | 11/2013 | Seguin |
| 8,585,755 B2 | 11/2013 | Chau |
| 8,591,575 B2 | 11/2013 | Cribier |
| 8,597,349 B2 | 12/2013 | Alkhatib |
| 8,603,159 B2 | 12/2013 | Seguin |
| 8,603,160 B2 | 12/2013 | Salahieh |
| 8,613,765 B2 | 12/2013 | Bonhoeffer |
| 8,623,074 B2 | 1/2014 | Ryan |
| 8,652,204 B2 | 2/2014 | Quill |
| 8,663,322 B2 | 3/2014 | Keraenen |
| 8,668,733 B2 | 3/2014 | Haug |
| 8,685,080 B2 | 4/2014 | White |
| 8,728,154 B2 | 5/2014 | Alkhatib |
| 8,747,459 B2 | 6/2014 | Nguyen |
| 8,764,820 B2 | 7/2014 | Dehdashtian |
| 8,795,357 B2 | 8/2014 | Yohanan |
| 8,801,776 B2 | 8/2014 | House |
| 8,808,356 B2 | 8/2014 | Braido |
| 8,828,078 B2 | 9/2014 | Salahieh |
| 8,834,563 B2 | 9/2014 | Righini |
| 8,840,661 B2 | 9/2014 | Manasse |
| 8,840,663 B2 | 9/2014 | Salahieh |

(56)　　　　References Cited

U.S. PATENT DOCUMENTS

| | | | |
|---|---|---|---|
| 8,876,894 B2 | 11/2014 | Tuval |
| 8,876,895 B2 | 11/2014 | Tuval |
| 8,940,040 B2 | 1/2015 | Shahriari |
| 8,945,209 B2 | 2/2015 | Bonyuet |
| 8,961,595 B2 | 2/2015 | Alkhatib |
| 8,974,523 B2 | 3/2015 | Thill |
| 8,974,524 B2 | 3/2015 | Yeung |
| 2002/0036220 A1 | 3/2002 | Gabbay |
| 2003/0023303 A1 | 1/2003 | Palmaz |
| 2003/0130726 A1 | 7/2003 | Thorpe |
| 2004/0049262 A1 | 3/2004 | Obermiller |
| 2004/0093075 A1 | 5/2004 | Kuehne |
| 2004/0111111 A1 | 6/2004 | Lin |
| 2004/0260389 A1 | 12/2004 | Case |
| 2005/0043790 A1 | 2/2005 | Seguin |
| 2005/0096726 A1 | 5/2005 | Sequin |
| 2005/0137682 A1 | 6/2005 | Justino |
| 2005/0143809 A1 | 6/2005 | Salahieh |
| 2005/0203605 A1 | 9/2005 | Dolan |
| 2005/0256566 A1 | 11/2005 | Gabbay |
| 2006/0008497 A1 | 1/2006 | Gabbay |
| 2006/0122692 A1 | 6/2006 | Gilad |
| 2006/0149360 A1 | 7/2006 | Schwammenthal |
| 2006/0161249 A1 | 7/2006 | Realyvasquez |
| 2006/0173532 A1 | 8/2006 | Flagle |
| 2006/0178740 A1 | 8/2006 | Stacchino |
| 2006/0195180 A1 | 8/2006 | Kheradvar |
| 2006/0206202 A1 | 9/2006 | Bonhoeffer |
| 2006/0241744 A1 | 10/2006 | Beith |
| 2006/0241745 A1 | 10/2006 | Solem |
| 2006/0259137 A1 | 11/2006 | Artof |
| 2006/0265056 A1 | 11/2006 | Nguyen |
| 2006/0276813 A1 | 12/2006 | Greenberg |
| 2006/0276874 A1 | 12/2006 | Wilson |
| 2007/0043435 A1 | 2/2007 | Seguin |
| 2007/0067029 A1 | 3/2007 | Gabbay |
| 2007/0093890 A1 | 4/2007 | Eliasen |
| 2007/0100435 A1 | 5/2007 | Case |
| 2007/0118210 A1 | 5/2007 | Pinchuk |
| 2007/0213813 A1 | 9/2007 | Von Segesser |
| 2007/0233228 A1 | 10/2007 | Eberhardt |
| 2007/0244545 A1 | 10/2007 | Birdsall |
| 2007/0288087 A1 | 12/2007 | Fearnot |
| 2008/0021552 A1 | 1/2008 | Gabbay |
| 2008/0039934 A1 | 2/2008 | Styrc |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey |
| 2008/0140189 A1 | 6/2008 | Nguyen |
| 2008/0147183 A1 | 6/2008 | Styrc |
| 2008/0154355 A1 | 6/2008 | Benichou |
| 2008/0154356 A1 | 6/2008 | Obermiller |
| 2008/0243245 A1 | 10/2008 | Thambar |
| 2008/0255662 A1 | 10/2008 | Stacchino |
| 2008/0262602 A1 | 10/2008 | Wilk |
| 2008/0269879 A1 | 10/2008 | Sathe |
| 2009/0099653 A1 | 4/2009 | Suri |
| 2009/0112309 A1 | 4/2009 | Jaramillo |
| 2009/0138079 A1 | 5/2009 | Tuval |
| 2009/0276027 A1 | 11/2009 | Glynn |
| 2010/0036484 A1 | 2/2010 | Hariton |
| 2010/0049306 A1 | 2/2010 | House |
| 2010/0087907 A1 | 4/2010 | Lattouf |
| 2010/0131055 A1 | 5/2010 | Case |
| 2010/0168778 A1 | 7/2010 | Braido |
| 2010/0168839 A1 | 7/2010 | Braido |
| 2010/0168844 A1 | 7/2010 | Toomes |
| 2010/0185277 A1 | 7/2010 | Braido |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau |
| 2010/0234940 A1 | 9/2010 | Dolan |
| 2010/0249911 A1 | 9/2010 | Alkhatib |
| 2010/0249923 A1 | 9/2010 | Alkhatib |
| 2011/0029072 A1 | 2/2011 | Gabbay |
| 2011/0054466 A1 | 3/2011 | Rothstein |
| 2011/0098800 A1 | 4/2011 | Braido |
| 2011/0098802 A1 | 4/2011 | Braido |
| 2011/0137397 A1 | 6/2011 | Chau |
| 2011/0172765 A1 | 7/2011 | Nguyen |
| 2011/0208283 A1 | 8/2011 | Rust |
| 2011/0264206 A1 | 10/2011 | Tabor |
| 2012/0035722 A1 | 2/2012 | Tuval |
| 2012/0041550 A1 | 2/2012 | Salahieh |
| 2012/0078347 A1 | 3/2012 | Braido |
| 2012/0101572 A1 | 4/2012 | Kovalsky |
| 2012/0123529 A1 | 5/2012 | Levi |
| 2012/0303116 A1 | 11/2012 | Gorman, III |
| 2013/0245753 A1 | 9/2013 | Alkhatib |
| 2013/0274873 A1 | 10/2013 | Delaloye |
| 2013/0304200 A1 | 11/2013 | Mclean |
| 2014/0121763 A1 | 5/2014 | Duffy |
| 2014/0155997 A1 | 6/2014 | Braido |
| 2014/0214159 A1 | 7/2014 | Vidlund |
| 2014/0222144 A1* | 8/2014 | Eberhardt ............. A61F 2/2418 |
| | | 623/2.38 |
| 2014/0228946 A1 | 8/2014 | Chau |
| 2014/0277411 A1 | 9/2014 | Börtlein |
| 2014/0303719 A1 | 10/2014 | Cox |
| 2014/0324164 A1 | 10/2014 | Gross |
| 2014/0343671 A1 | 11/2014 | Yohanan |
| 2014/0350668 A1 | 11/2014 | Delaloye |
| 2014/0350669 A1 | 11/2014 | Gillespie |

FOREIGN PATENT DOCUMENTS

| | | |
|---|---|---|
| DE | 202008009610 U1 | 12/2008 |
| EP | 0732088 A2 | 9/1996 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 2537487 A1 | 12/2012 |
| EP | 3107496 B1 | 7/2018 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 0149213 A2 | 7/2001 |
| WO | 0156500 A2 | 8/2001 |
| WO | 2001054625 A1 | 8/2001 |
| WO | 2001076510 A2 | 10/2001 |
| WO | 2002036048 A1 | 5/2002 |
| WO | 0247575 A2 | 6/2002 |
| WO | 2003047468 A1 | 6/2003 |
| WO | 2005062980 A2 | 7/2005 |
| WO | 2005070343 A1 | 8/2005 |
| WO | 2006073626 A2 | 7/2006 |
| WO | 2007058857 A2 | 5/2007 |
| WO | 2009094188 A2 | 7/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2013037519 A1 | 3/2013 |
| WO | 2013106585 A1 | 7/2013 |
| WO | 2015012671 A1 | 1/2015 |
| WO | 2015077274 A1 | 5/2015 |
| WO | 2015126712 A1 | 8/2015 |

OTHER PUBLICATIONS

Andersen, Henning Rud, Transluminal Catheter Implanted Prosthetic Heart Valves, International Journal of Angiology 7:102-106 (1998).

Braido, et al., U.S. Appl. No. 29/375,243, filed Sep. 20, 2010, titled "Surgical Stent Assembly".

(56)          References Cited

OTHER PUBLICATIONS

Buellesfeld, et al., "Treatment of paravalvular leaks through inverventional techniques," Multimed Man Cardiothorac Surg., Department of Cardiology, Ben University Hospital, pp. 1-8, Jan. 2011.

Buesseler et al., "Bowed Runners for Paravalvular Leak Protection," U.S. Appl. No. 61/941,024, filed Feb. 18, 2014.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Dewey, et al., "Transapical Aortic Valve Implantation: An Animal Feasibility Study", The Annals of Thoracic Surgery, vol. 82, No. 1, Jul. 2006, pp. 110-116.

Gössl et al., "Percutaneous Treatment of Aortic and Mitral Valve Paravalvular Regurgitation", Current Cardiology Reports, vol. 15, No. 8, Aug. 2013, pp. 1-8.

Heat Advisor, "Heart Repairs Without Surgery: Minimally Invasive Procedures Aim to Correct Valve Leakage", Technology Frontier, Sep. 2004, pp. 4-5.

Hijazi et al., Transcatheter Valve Repair, CRC Press, Jan. 2006, pp. 165-186.

Hourihan, et al., "Transcatheter Umbrella Closure of Valvular and Paravalvular Leaks," Journal of the American College of Cardiology, vol. 20, No. 6, pp. 1371-1377, Nov. 1992.

Huber, et al., "Direct-Access Valve Replacement: A Novel Approach for Off-Pump Valve Implantation Using Valved Stents", Journal of the American College of Cardiology, vol. 46, No. 2, Jul. 2005, pp. 366-370.

International Search Report for Application No. PCT/US2015/015537 dated May 4, 2015.

Knudsen LL, Andersen HR, Hasenkam JM. Catheter-Implanted Prosthetic Heart Valves: Transluminal catheter Implantation of a new expandable artificial heart valve in the descending thoracic aorta in isolated vessels and closed chest pigs. The International Journal of Artificial Organs. May 1993;16(5):253-62.

Mack, "Minimally invasive cardiac surgery", Surgical Endoscopy, 2006, 20:S488-S492, DOI: 10.1007/s00464-006-0110-8, presented Apr. 24, 2006.

Moazami et al., "Transluminal Aortic Valve Placement: A Feasibility Study With a Newly designed Collapsible Aortic Valve.", ASAIO Journal, (19960900), vol. 42, pp. M381-M385, XP000683605.

Rodriguez et al., "Guidance of Treatment of Pehvalvular Prosthetic Leaks", Current Cardiology Reports, vol. 16, No. 1, Nov. 2013, pp. 1-6.

Rohde, et al., "Resection of Calcified Aortic Heart Leaflets In Vitro by Q-Switched 2 pm Microsecond Laser Radiation", Journal of Cardiac Surgery, 30(2):157-62. Feb. 2015.

Samuel V. Lichtenstein et al., Transapical Transcatheter Aortic Valve Implantation in Humans, Circulation, Jul. 2006, pp. 591-596, vol. 114.

Samuel V. Lichtenstein, "Closed heart surgery: Back to the future", The Journal of Thoracic and Cardiovascular Surgery, vol. 131, No. 5, pp. 941-943, May 2006.

Swiatkiewicz, et al., "Percutaneous closure of mitral perivalvular leak," Kardiologia Polska, vol. 67, No. 7, pp. 762-764, Jul. 2009.

TH. Walther et al., "Transapical Approach for Sutureless Stent-Fixed Aortic Valve Implantation: Experimental Results", European Journal of Cardio-Thoracic Surgery, vol. 29, No. 5, May 2006, pp. 703-708.

Webb et al., "Percutaneous Aortic Valve Implantation Retrograde From the Femoral Artery", Circulation, published online Feb. 2006, pp. 842-850, vol. 113, American Heart Association, Dallas, TX, USA.

Zegdi, Rachid, MD, PhD et al., "Is It Reasonable to Treat All Calcified Stenotic Aortic Valves With a Valved Stent?" 579-584, J. of the American College of Cardiology, vol. 51. No. 5, Feb. 5, 2008.

* cited by examiner

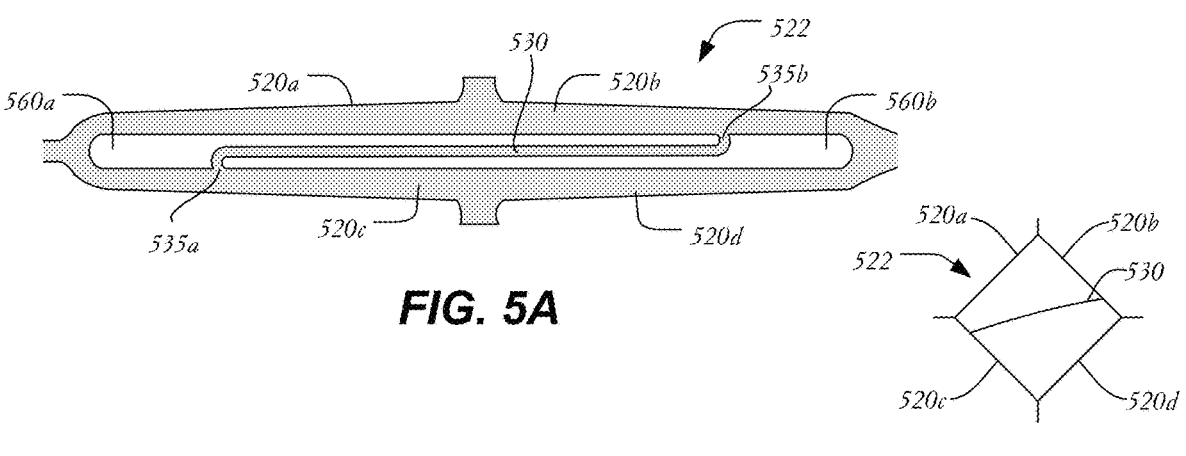
FIG. 5A
FIG. 5B
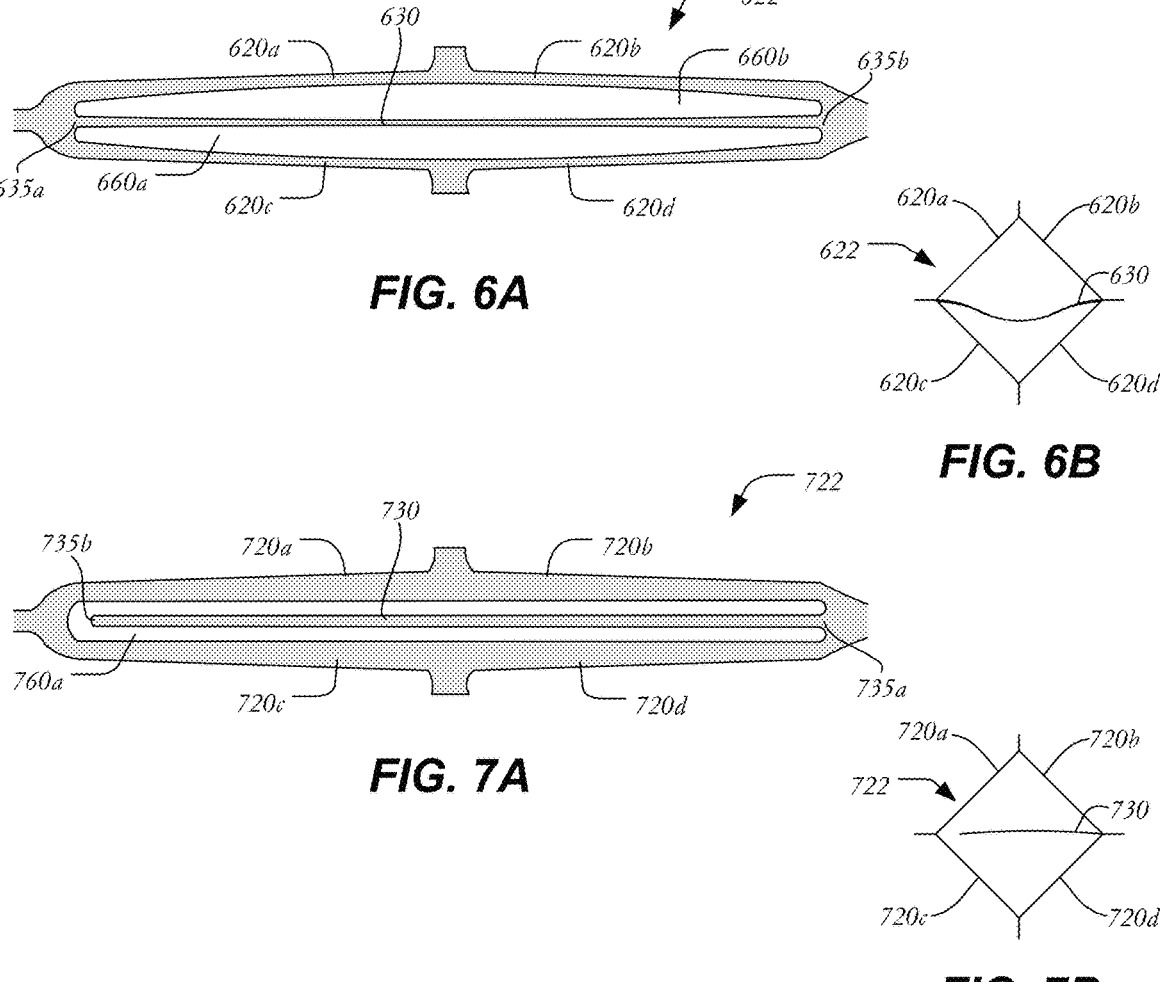
FIG. 6A
FIG. 6B
FIG. 7A
FIG. 7B

BOWED RUNNERS FOR PARAVALVULAR LEAK PROTECTION

CROSS-REFERENCE TO RELATED APPLICATIONS

This application is a divisional of U.S. application Ser. No. 15/119,566, filed Aug. 17, 2016, which is a national phase entry under 35 U.S.C. § 371 of International Application No. PCT/US2015/015537 filed Feb. 12, 2015, published in English, which claims priority from U.S. Provisional Patent Application No. 61/941,024, filed Feb. 18, 2014, all of which are incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve for replacing a native valve includes a stent including a plurality of struts forming cells, the stent having a collapsed condition and an expanded condition. A valve assembly is disposed within the stent, the valve assembly including a plurality of leaflets and a cuff. At least one runner is coupled to a cell, the at least one runner being configured to transition from a first configuration to a second configuration when the stent moves from the collapsed condition to the expanded condition, the at least one runner projecting radially outwardly from the cell in the second configuration.

In some embodiments, a prosthetic heart valve for replacing a native valve includes a stent including a plurality of struts forming cells, the stent having a collapsed condition and an expanded condition. A valve assembly is disposed within the stent, the valve assembly including a plurality of leaflets and a cuff. A nested strut is coupled to a cell, the nested strut being configured to transition from a first configuration to a second configuration when the stent moves from the collapsed condition to the expanded condition, the nested strut projecting radially outwardly from the cell in the second configuration.

BRIEF DESCRIPTION OF THE DRAWINGS

Various embodiments in accordance with the present disclosure will now be described with reference to the appended drawings. It is to be appreciated that these drawings depict only some embodiments and are therefore not to be considered limiting of its scope.

FIGS. 5A-10B are enlarged highly schematic partial side views of several variations of collapsed cells having bowed runners and their respective shapes in the expanded configurations;

DETAILED DESCRIPTION

Despite various improvements that have been made to the collapsible prosthetic heart valve delivery process, conventional devices suffer from some shortcomings. For example, with conventional self-expanding valves, the clinical success of the valve is dependent on accurate deployment and anchoring. Inaccurate deployment and anchoring of the valve increases risks, such as those associated with valve migration, which may cause complications due to the obstruction of the left ventricular outflow tract. Inaccurate deployment and anchoring may also result in the leakage of blood between the implanted heart valve and the native valve annulus, commonly referred to as paravalvular leakage (also known as "perivalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient or performing an additional valve-in-valve procedure. Removing a fully deployed heart valve increases the length of the procedure as well as risks. Thus, methods and devices are desirable that would reduce the need to remove a prosthetic heart valve from a patient. Methods and devices are also desirable that would reduce the likelihood of paravalvular leakage due to gaps between the implanted heart valve and patient tissue.

There therefore is a need for further improvements to the devices, systems, and methods for positioning and sealing collapsible prosthetic heart valves. Specifically, there is a need for further improvements to the devices, systems, and methods for accurately implanting a prosthetic heart valve. Among other advantages, the present disclosure may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

Figure 1:
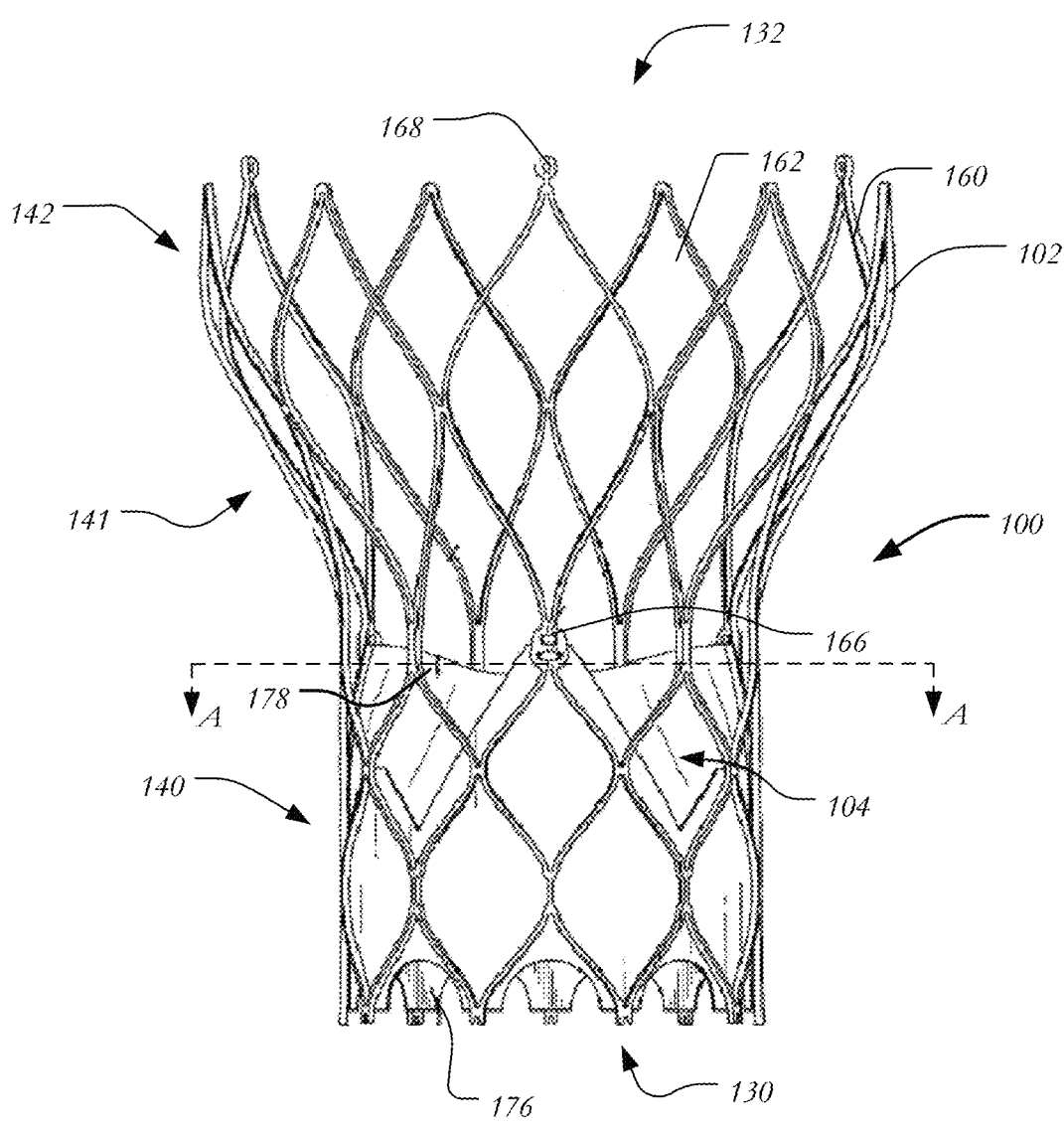
FIG. 1 is a side elevational view of a conventional prosthetic heart valve.

The sealing elements of the present disclosure may be used in connection with collapsible prosthetic heart valves. FIG. 1 shows one such collapsible stent-supported prosthetic heart valve 100 including a stent 102 and a valve assembly 104 as is known in the art. Prosthetic heart valve 100 is designed to replace a native tricuspid valve of a patient, such as a native aortic valve. It should be noted that while the disclosures herein relate predominantly to prosthetic aortic valves having a stent with a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141 and aortic section 142 adjacent distal end 132. Annulus section 140 may have a relatively small cross-section in the expanded configuration, while aortic section 142 may have a relatively large cross-section in the expanded configuration. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably secured to stent 102 in annulus section 140. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing elements of the present disclosure may be used may have a greater or lesser number of leaflets.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, Polyethylene terephthalate (PET), ultra-high-molecular-weight polyethylene (UHMWPE), or polytetrafluoroethylene (PTFE).

Leaflets 178 may be attached along their belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed configuration. The delivery device may be introduced into a patient using a transfemoral, transapical, transaortic, transsubclavian, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2:
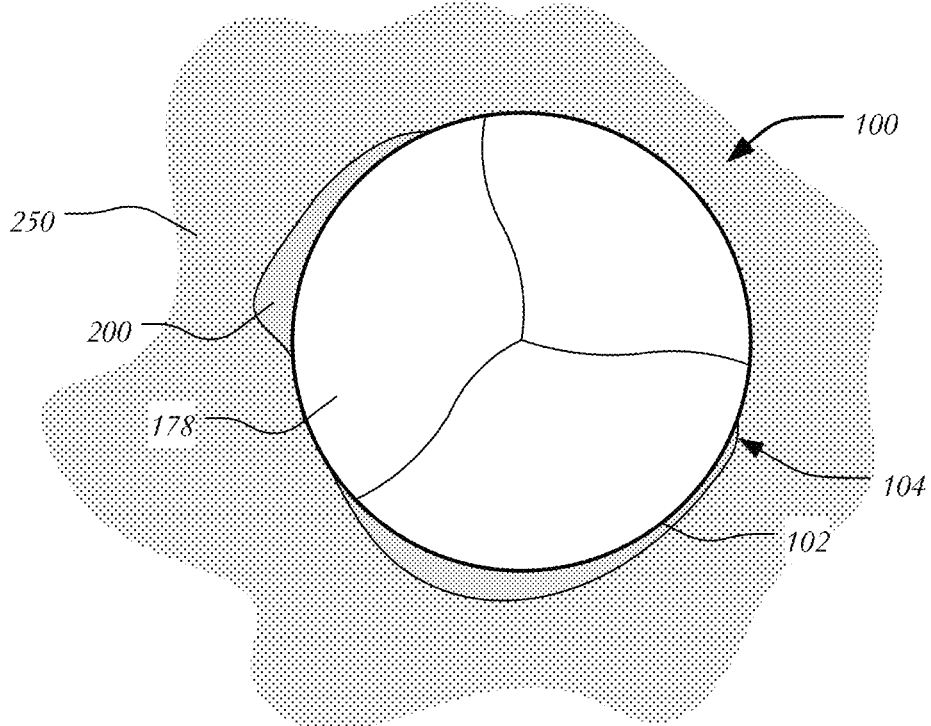
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, valve assembly 104 has a substantially circular cross-section which is disposed within the non-circular native valve annulus 250. At certain locations around the perimeter of heart valve 100, gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to unresected native leaflets.

Figure 3A:
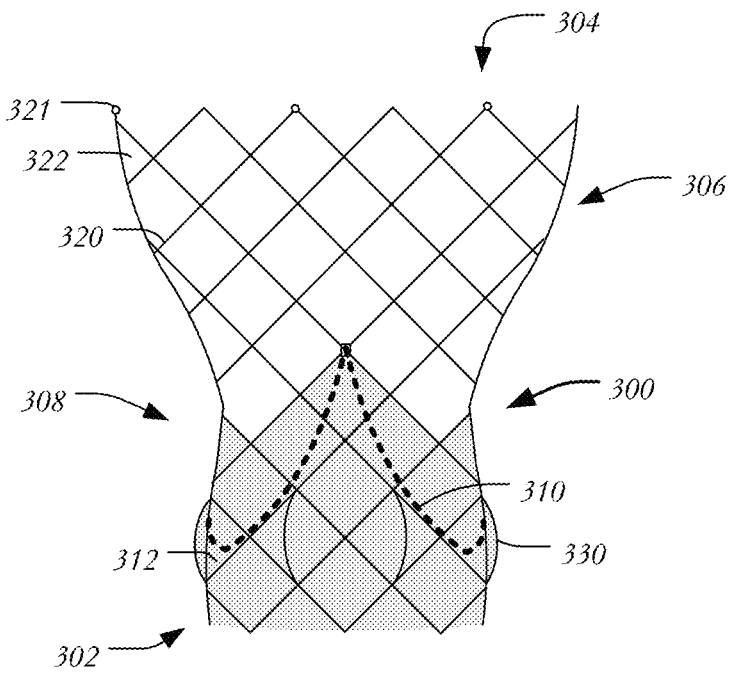
FIG. 3A is a highly schematic side view of one embodiment of a heart valve having bowed runners intended to fill irregularities between the heart valve and the native valve annulus.

FIG. 3A illustrates one embodiment of heart valve 300 intended to fill the irregularities between the heart valve and native valve annulus 250 shown in FIG. 2. Heart valve 300 extends between proximal end 302 and distal end 304, and may generally include stent 306 and valve assembly 308 having a plurality of leaflets 310 and cuff 312. Heart valve 300 may be formed of any of the materials and in any of the configurations described above with reference to FIG. 1.

Stent 306 may include a plurality of struts 320. Certain struts 320 may terminate in retaining elements 321 at distal end 304. Struts 320 may come together to form cells 322 connected to one another in one or more annular rows around the stent. Connected to struts 320 are a plurality of runners 330, which are additional struts that bow or bulge out radially where stent 306 is expanded, as will be described in greater detail with reference to FIGS. 3B and 3C.

Figures 3B, 3C, 3D:
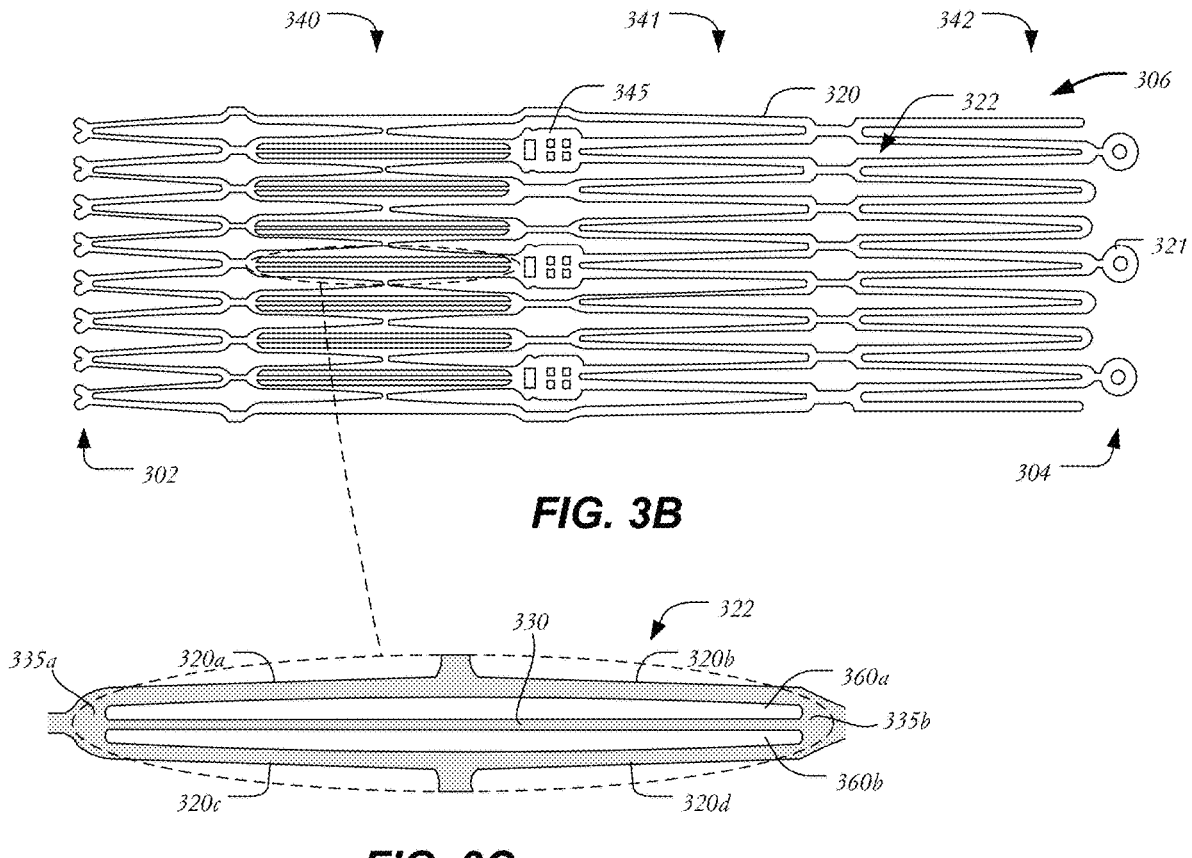
FIG. 3B is a developed view of the stent of the heart valve of FIG. 3A in the collapsed configuration.
FIGS. 3C and 3D are enlarged highly schematic partial views of a cell having a bowed runner in the collapsed configuration and expanded configuration, respectively.

In order to better appreciate the attachment and placement of runners 330, stent 306 is shown in FIG. 3B in its collapsed configuration. For the sake of clarity, valve assembly 308 is not shown in this figure. In the collapsed configuration of stent 306, each of cells 322 is also collapsed. Stent 306 extends from proximal or annulus end 302 of heart valve 300 to distal or aortic end 304, and includes annulus section 340 adjacent proximal end 302, aortic section 342 adjacent distal end 304, and transition section 341 between annulus section 340 and aortic section 342. Commissure features 345 may be positioned entirely within annulus section 340 or at the juncture of annulus section 340 and transition section 341 as shown.

One or more cells 322 may include runners 330. An enlarged partial side view of cell 322 including runner 330 is shown in FIG. 3C. Four struts 320a, 320b, 320c, 320d may join to form cell 322, each strut being attached to two adjacent struts. In the collapsed configuration of stent 306, cell 322 may be stadium-shaped as shown. In the expanded configuration of stent 306, cell 322 may shorten in the length direction of stent 306 between proximal end 302 and distal end 304, and struts 320 may generally form a diamond shape (FIG. 3D).

Runners 330 may extend from first attachment end 335a where struts 320a and 320c meet to second attachment end 335b where struts 320b and 320d meet, and may be affixed to stent 306 by welding, adhesive, or any other suitable technique known in the art. Moreover, instead of being separately formed and affixed to stent 306 at attachment ends 335a, 335b, runners 330 may be integrally formed with stent 306, such as by laser cutting both stent 306 and runners 330 from the same tube. Additionally, runners 330 may be formed of a shape memory material such as those described above for forming stent 102 of FIG. 1, and may have a substantially linear configuration in the collapsed configuration of heart valve 300 (FIG. 3C) and a curved configuration in the expanded configuration of heart valve 300 (FIG. 3D).

In the collapsed configuration, runner 330 may bisect cell 322 into first portion 360a and second portion 360b. As cell 322 foreshortens in the expanded configuration of heart valve 300, the unchanged length of runner 330 causes the runner to bow or deflect outwardly of the curved surface defined by struts 320a, 320b, 320c, 320d. Stent 306 may also be heat set such that struts 320 and runner 330 return to a predetermined shape in the fully expanded configuration (e.g., when no external forces are applied thereto). When cuff 312 (FIG. 3A) is coupled to the abluminal surface of annulus section 340 of stent 306, the cuff is substantially tubular when runners 330 are not bowed outwardly. When runners 330 bow outwardly in expansion of heart valve 300, they form protuberances in cuff 312 to help seal heart valve 300 within the native valve annulus.

Figures 4A, 4B:
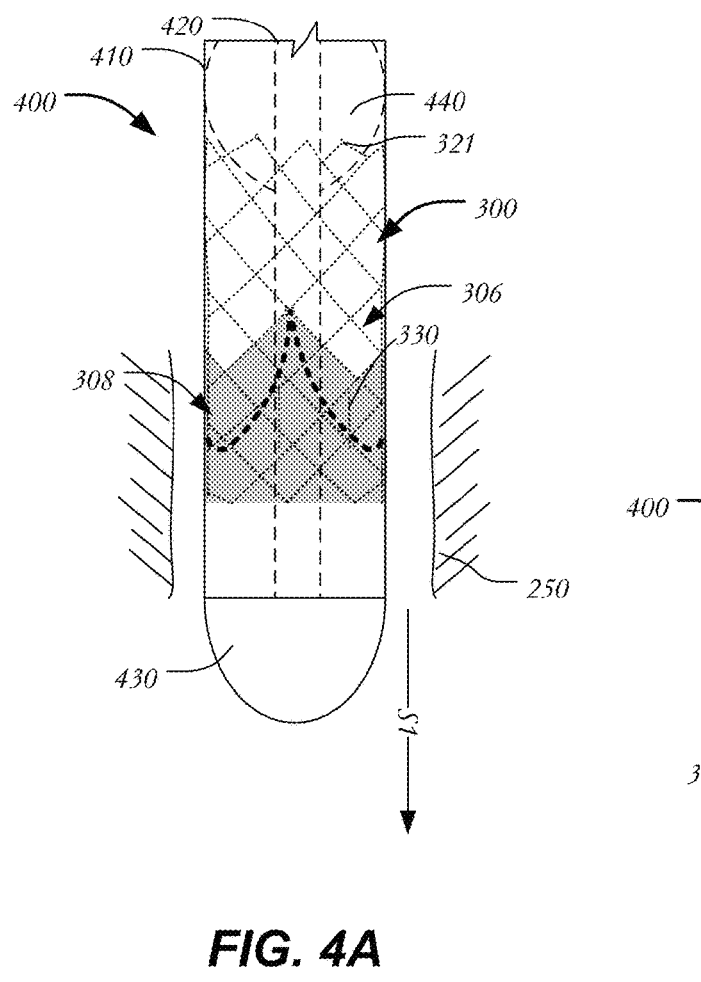
FIGS. 4A-D are highly schematic side views of one method of delivering and deploying the heart valve of FIG. 3A within the native valve annulus.

A method of delivering and implanting heart valve 300 will now be described with reference to FIGS. 4A-D. A delivery system 400 may be used to deliver and deploy heart valve 300 in native valve annulus 250, and may generally include sheath 410, shaft 420, atraumatic tip 430 and hub 440. Sheath 410 may be slidable relative to shaft 420. Heart valve 300, including stent 306, valve assembly 308 and runners 330, may be disposed within sheath 410 about shaft 420 (FIG. 4A). Hub 440 may be coupled to shaft 420 and configured to mate with retaining elements 321 of heart valve 300. Runners 330 of heart valve 300 may be disposed in the linear configuration of FIG. 3C, substantially parallel to sheath 410, during delivery. Specifically, though runners 330 are configured to return to their curved configuration, they may be kept substantially linear by being constrained within sheath 410. By doing so, heart valve 300 may be delivered to the native valve annulus using delivery system 400 without increasing the radius of sheath 410, avoiding the need to increase the crimp profile of the heart valve within delivery system 400. A large delivery system may be incapable of being passed through the patient's vasculature, while a delivery system having a heart valve with a smaller crimp profile may be easier to navigate through a patient's body and may also reduce the length of the implantation procedure. In the example shown in FIGS. 4A-D, delivery system 400 is delivered from the aorta toward the left ventricle as indicated by arrow S1. If heart valve 300 or delivery system 400 includes echogenic materials, such materials may be used to guide delivery system 400 to the appropriate position using the assistance of three-dimensional echocardiography to visualize heart valve 300 within the patient. Alternative visualization techniques known in the art are also contemplated herein.

Figures 4C, 4D:
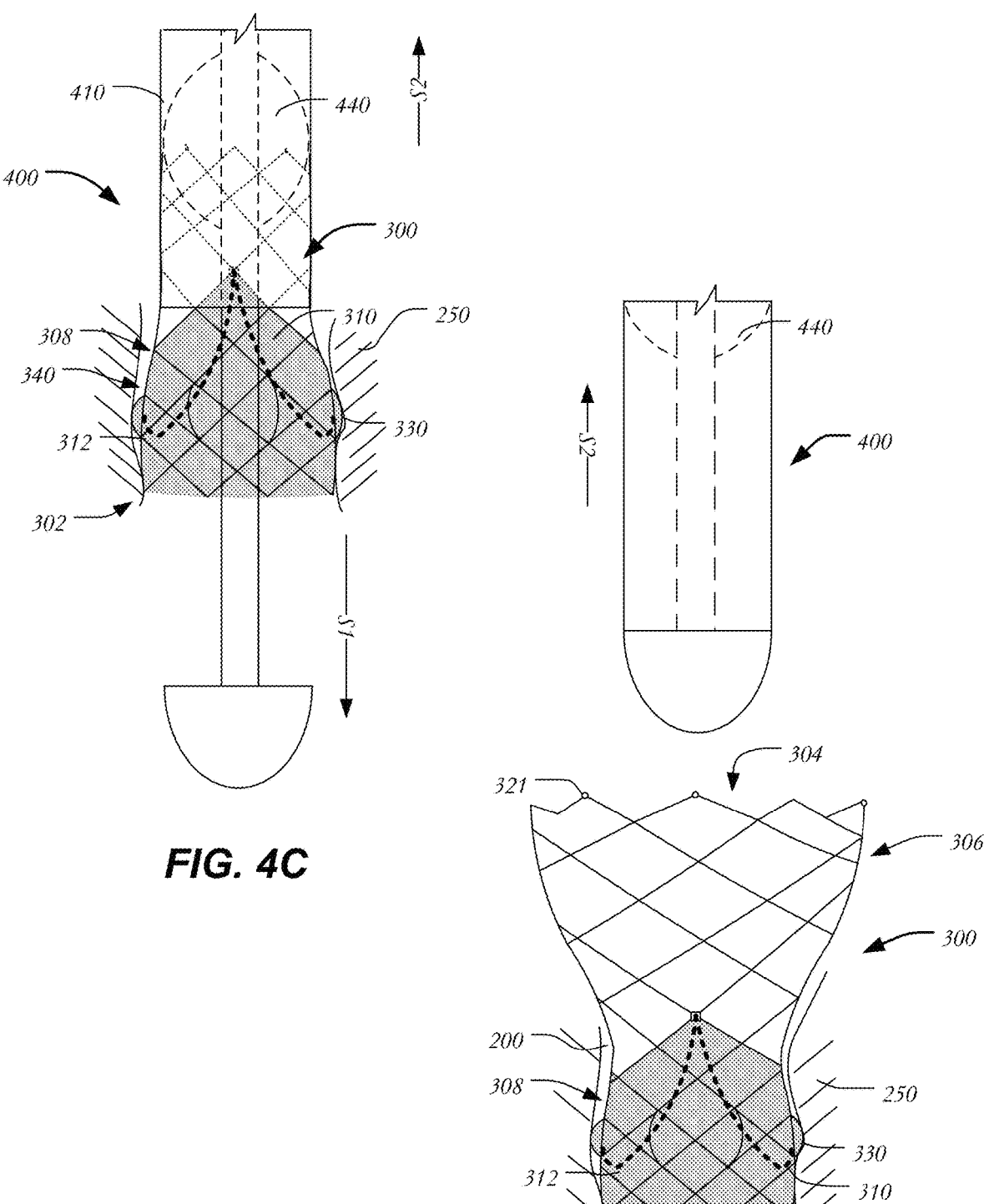

When delivery system 400 has reached the proper location (e.g., atraumatic tip 430 is just past native valve annulus 250), atraumatic tip 430 may be advanced slightly in the direction of arrow S1 toward the left ventricle by pushing shaft 420 toward atraumatic tip 430 while holding sheath 410 in place, which serves to decouple atraumatic tip 430 from sheath 410 (FIG. 4B). Sheath 410 may then be retracted in the direction of arrow S2 toward the aorta. With sheath 410 slightly retracted, heart valve 300 begins to emerge from the sheath. As sheath 410 is further retracted in the direction of arrow S2, more of heart valve 300 is exposed until annulus section 340 is fully exposed and runners 330 become bowed (FIG. 4C). Thus, sheath 410 may be retracted until heart valve 300 is free to self-expand within native valve annulus 250. While heart valve 300 is partially deployed (e.g., a portion of heart valve 300 is outside sheath 410, but heart valve 300 is not fully detached from delivery system 400), if it appears that heart valve 300 needs to be recaptured and redeployed due to, for example, improper positioning or orientation, sheath 410 may be slid over shaft 420 in the direction of arrow S1 to recapture heart valve 300 within sheath 410. During recapture, sheath 410 may push against bowed runners 330 to straighten them to the linear configuration shown in FIG. 3C. This process may be repeated until heart valve 300 is properly positioned and deployed within native valve annulus 250.

After sheath 410 has been fully retracted to expose heart valve 300, runners 330, now in their bowed or curved configuration, push cuff 312 outwardly against native valve annulus 250 and occlude gaps 200 between heart valve 300 and native valve annulus 250, thereby reducing or eliminating the amount of blood that passes around heart valve 300 through gaps 200 (FIG. 4D). Retaining elements 321 of heart valve 300 may decouple from hub 440 as heart valve 300 fully expands, atraumatic tip 430 may be retracted through heart valve 300 in the direction of arrow S2 and delivery system 400 may be removed from the patient.

Several variations of runners are described with reference to FIGS. 5A-10B. In each variation, a collapsed cell is shown along with a schematic of the cell in the expanded configuration. As used herein the terms expanded and collapsed may refer to the configurations of a cell, a stent, a heart valve and a valve assembly interchangeably.

FIG. 5A shows cell 522 of a stent having four struts 520*a*, 520*b*, 520*c*, 520*d*, each strut being attached to two adjacent struts. In the collapsed configuration of the stent, cell 522 may be stadium-shaped as shown (FIG. 5A). Runner 530 may extend between two attachment ends 535*a*, 535*b*. Specifically, runner 530 may be joined to third strut 520*c* at first attachment end 535*a* and to diagonally-opposed second strut 520*b* at second attachment end 535*b*. Runner 530 may diagonally divide cell 522 substantially equally into first portion 560*a* and second portion 560*b* in the collapsed configuration. When cell 522 is placed in the expanded configuration (FIG. 5B), the cell may form a substantially diamond shape, with runner 530 stretching diagonally from second strut 530*b* to third strut 530*c* across the cell. Because attachment ends 535*a*, 535*b* are closer to one another in the expanded configuration than in the collapsed configuration, runner 530 may bow outwardly to form a protuberance.

FIG. 6A shows cell 622 of a stent having four struts 620*a*, 620*b*, 620*c*, 620*d*, each strut being attached to two adjacent struts. Runner 630 may extend between two attachment ends 635*a*, 635*b* located at junctions of two struts (e.g., attachment end 635*a* is at the junction of struts 620*a* and 620*c*, while attachment end 635*b* is at the junction of struts 620*b* and 620*d*) and bisect cell 622 into substantially equal first portion 660*a* and second portion 660*b* in the collapsed configuration. Runner 630 may be tapered as shown, having a larger width at attachment ends 635*a*, 635*b* than at its middle. A tapered runner 630 may provide added flexibility and may be easier to heat set so that it readily returns to the bowed configuration when cell 622 is expanded, as shown in FIG. 6B.

FIG. 7A shows cell 722 of a stent having four struts 720*a*, 720*b*, 720*c*, 720*d*, each strut being attached to two adjacent struts. Unlike cell 322, runner 730 is joined to cell 722 at a single attachment end 735*a* only and is able to deflect at free end 735*b* opposite attachment end 735*a*. It will be understood that the single point of attachment may be disposed at any of struts 720*a*, 720*b*, 720*c*, 720*d* or at the intersection of any two struts (e.g., at the intersection of second strut 720*b* and fourth strut 720*d* as shown or at the opposite end at the intersection of first strut 720*a* and third strut 720*c* or at the intersection of first strut 720*a* and second strut 720*b* or at the opposite end at the intersection of third strut 720*c* and fourth strut 720*d*). In the collapsed configuration, runner 730 fills a portion of cell 722 so that a U-shaped cutout 760*a* is formed within cell 722. In the expanded configuration (FIG. 7B), runner 730 is capable of bowing radially outwardly to provide paravalvular sealing.

Figures 8A, 8B, 9A, 9B, 10A, 10B:
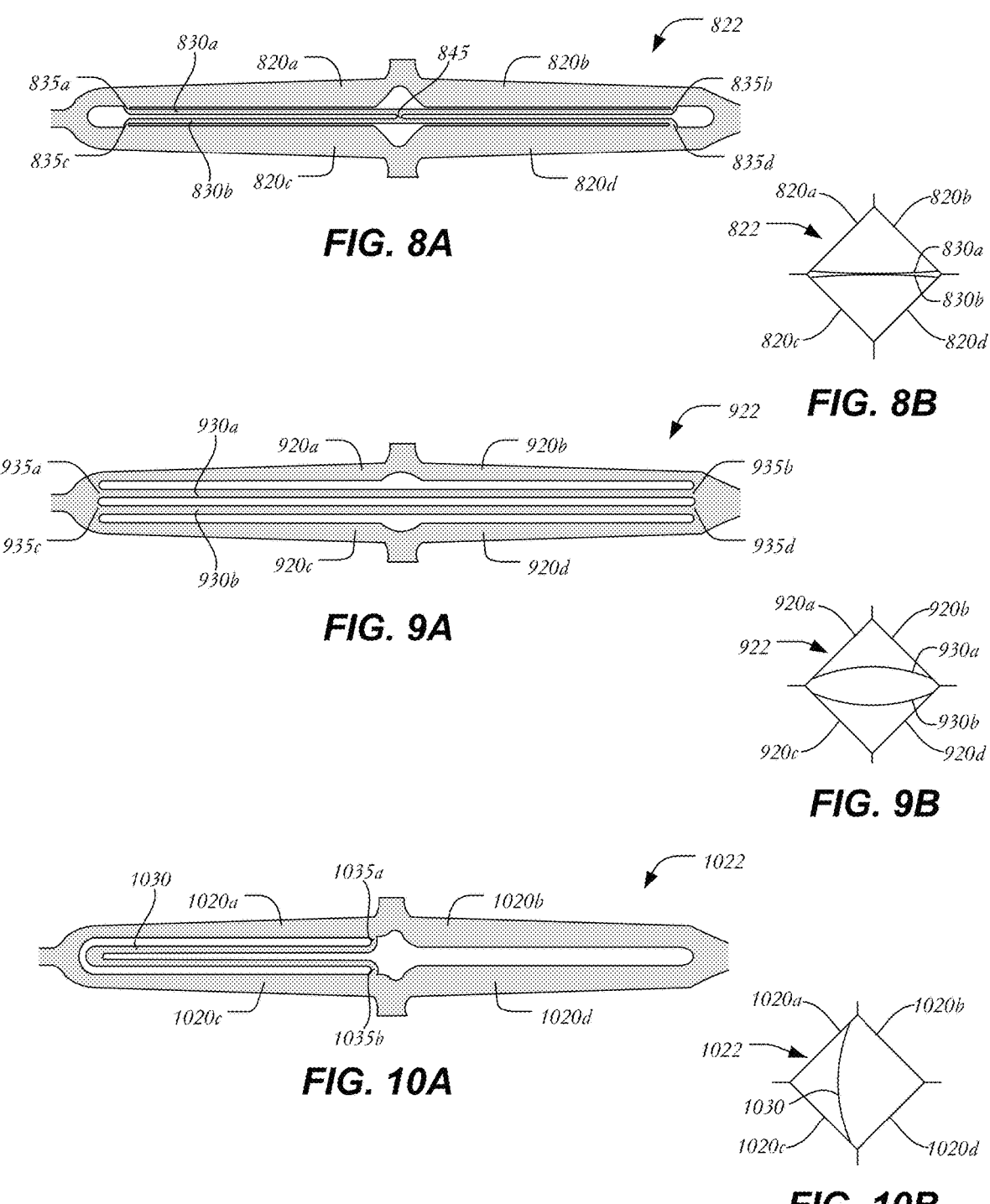

FIG. 8A shows cell 822 of a stent having four struts 820*a*, 820*b*, 820*c*, 820*d*, each strut being attached to two adjacent struts. Cell 822 includes a pair of runners 830*a*, 830*b* that are substantially parallel to one another in the collapsed configuration. First runner 830*a* is coupled to first strut 820*a* at first attachment end 835*a* and to second strut 820*b* at second attachment end 835*b*, while second runner 830*b* is coupled to third strut 820*c* at third attachment end 835*c* and to fourth strut 820*d* at fourth attachment end 835*d*. Moreover, first and second runners 830*a*, 830*b* are coupled to one another at midpoint 845, which keeps runners 830*a*, 830*b* close together along a midline of the diamond shaped cell 822 in the expanded configuration (FIG. 8B). Twin runners 830*a*, 830*b* may provide a larger support surface over which a cuff may be stretched to better seal a heart valve within a native valve annulus.

FIG. 9A shows another variation having twin runners. Cell 922 includes four struts 920*a*, 920*b*, 920*c*, 920*d*, each strut being attached to two adjacent struts. Cell 922 includes a pair of runners 930*a*, 930*b* that are substantially parallel to one another in a collapsed configuration. First runner 930*a* is coupled to the junction of first strut 920*a* and third strut 920*c* at first attachment end 935*a* and to the junction of second strut 920*b* and fourth strut 920*d* at second attachment end 935*b*, while second runner 930*b* is coupled to the same two junctions at third attachment end 935*c* and fourth attachment end 935*d*. Runners 930*a*, 930*b* are not joined to one another except for having attachment ends near one another. When cell 922 expands, runners 930*a*, 930*b* bow outwardly and separate to provide scaffolding upon which a cuff may be stretched (FIG. 9B). Instead of the cuff being stretched out over a single bowed runner or dual bowed runners attached at a midpoint, stretching the cuff over twin bowed runners that are spaced apart from one another provides a greater support area. Thus, this separation of bowed runners 930*a*, 930*b* may provide a more uniform protuberance for better sealing of a heart valve within the native valve annulus.

Another variation, shown in FIG. 10A, includes cell 1022 having four struts 1020*a*, 1020*b*, 1020*c*, 1020*d*, each strut being attached to two adjacent struts. Runner 1030 is formed as a U-shaped nested strut in the collapsed configuration, being attached to two adjacent struts 1020*a*, 1020*c* at attachment ends 1035*a*, 1035*b*, respectively. In the expanded configuration, runner 1030 bows radially outwardly to form a protuberance (FIG. 10B). Because bowed runner 1030 is attached to adjacent struts 1020*a*, 1020*c* and stretches between two attachment points at about the same longitudinal position, in the expanded configuration, bowed runner 1030 extends laterally across cell 1022.

Additionally, runners may be provided at a variety of locations on a stent. For example, in FIG. 11A, heart valve 1100A extends between proximal end 1102 and distal end 1104, and may generally include stent 1106 and valve assembly 1108 having a plurality of leaflets 1110 and cuff 1112. Heart valve 1100 may be formed of any of the materials and in any of the configurations described above with reference to FIG. 1.

Figures 11A, 11B, 11C:
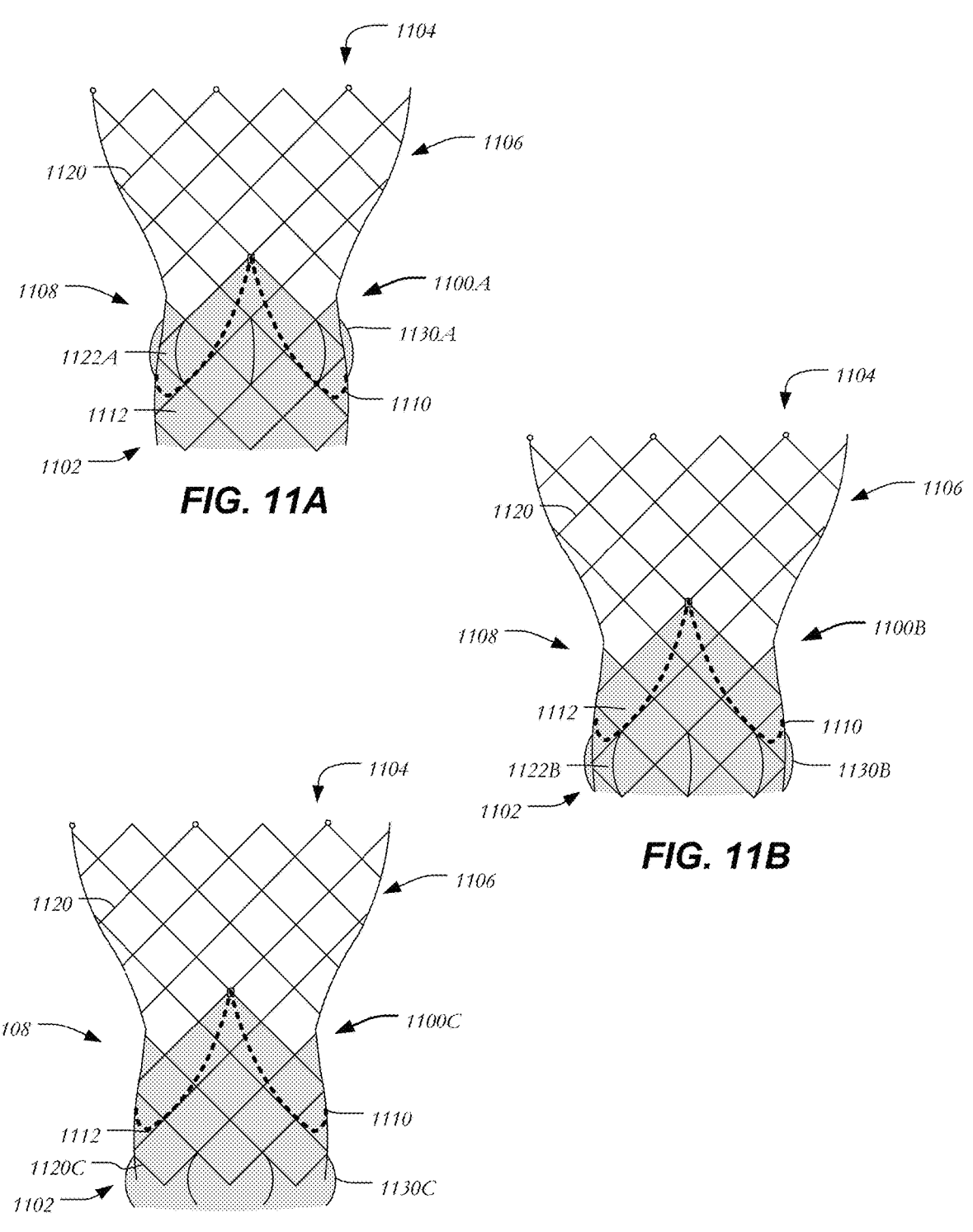
FIGS. 11A-C are enlarged highly schematic side views of heart valves having bowed runners at various longitudinal positions.

Stent 1106 may include a plurality of struts 1120, which may come together to form cells, such as cell 1122A, connected to one another in one or more annular rows around the stent. Connected to struts 1120 are a plurality of runners 1130A, which are additional struts that bow or bulge out radially when stent 1106 is expanded, as will be described in greater detail with reference to FIGS. 11B and 11C. As shown in FIG. 11A, runners 1130A are attached to the third full row of cells 1122A from proximal end 1102 so that at least a portion of each runner is disposed radially outward of leaflets 1110. In a second variation, shown in FIG. 11B, heart valve 1100B includes runners 1130B attached to the first full row of cells 1122B from proximal end 1102. In yet another variation, shown in FIG. 11C, heart valve 1100C includes runners 1130C attached to the bottommost struts 1120C so that they extend proximally of the proximal end 1102 of stent 1106. It will be understood that the longitudinal position of runners 1130 may be varied anywhere within the annulus section and/or transition section. Additionally, multiple rows of runners may be disposed on stent 1106. Moreover, each cell in an annular row of cells need not include a runner. Thus, there may be more runners in one annular row of cells than in another annular row of cells.

Figure 12:
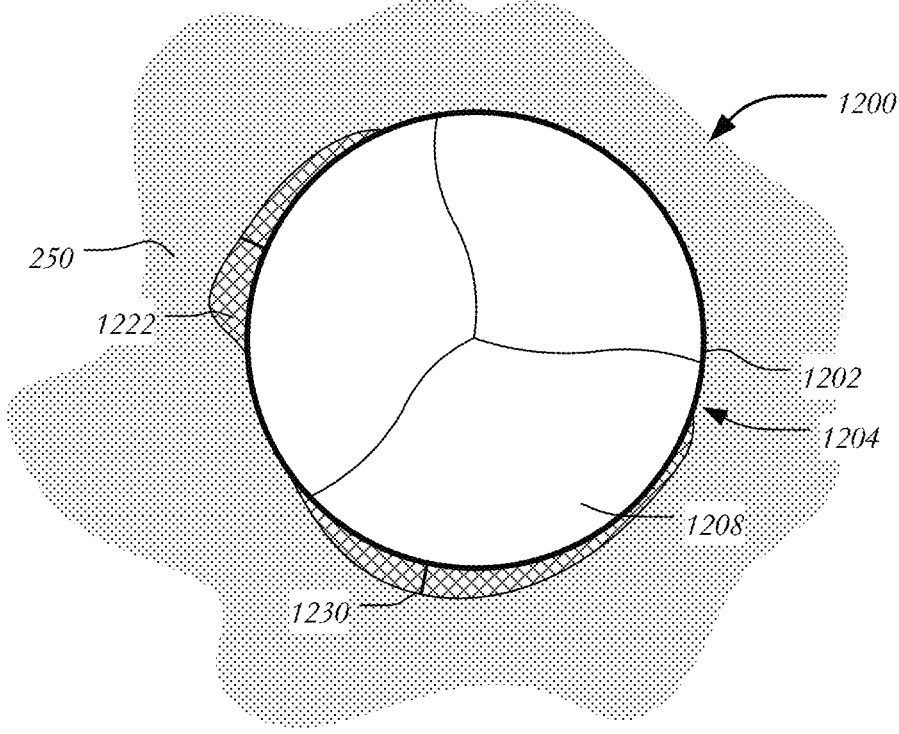
FIG. 12 is a highly schematic cross-sectional view of a heart valve having bowed runners disposed within a native valve annulus.

FIG. 12 is a highly schematic cross-sectional view showing heart valve 1200 having stent 1202, valve assembly 1204 including leaflets 1208 and a cuff 1222, and bowed runners 1230 supporting portions of cuff 1222. As seen in FIG. 12, bowed runners 1230 extend radially outward from stent 1202 to press cuff 1222 into gaps 200 shown in FIG. 2. Cuff 1222 may be capable of promoting tissue growth between heart valve 1200 and native valve annulus 250. For example, cuff 1222 may be innately capable or promoting tissue growth and/or may be treated with a biological or chemical agent to promote tissue growth, further enabling it to seal the heart valve within the native valve annulus. When bowed runners 1230 are functioning properly, heart valve 1200 will be adequately sealed within native valve annulus 250 so that blood flows through leaflets 1208 of valve assembly 1204, and so that blood flow through any gaps formed between heart valve 1200 and native valve annulus 250 is limited or reduced.

While the devices disclosed herein are for use in connection with heart valve stents having a particular shape, the stents could have different shapes, such as a flared or conical annulus section, a less-bulbous aortic section, and the like, as well as a differently shaped transition section. Additionally, though the runners have been described in connection with expandable transcatheter aortic valve replacement, they may also be used in connection with other expandable cardiac valves, as well as with surgical valves, sutureless valves and other devices in which it is desirable to create a seal between the periphery of the device and the adjacent body tissue.

Moreover, although the disclosures herein are for particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present claims.

It will be appreciated that the various dependent claims and the features set forth therein can be combined in different ways than presented in the initial claims. It will also be appreciated that the features described in connection with individual embodiments may be shared with others of the described embodiments.

In some embodiments, a prosthetic heart valve for replacing a native valve includes a stent including a plurality of struts forming cells, the stent having a collapsed condition and an expanded condition. A valve assembly is disposed within the stent, the valve assembly including a plurality of leaflets and a cuff. At least one runner is coupled to a cell, the at least one runner being configured to transition from a first configuration to a second configuration when the stent moves from the collapsed condition to the expanded condition, the at least one runner projecting radially outwardly from the cell in the second configuration.

In some examples, the at least one runner is substantially linear in the first configuration, and/or the at least one runner is bowed in the second configuration, and/or the at least one runner pushes the cuff radially outwardly when the at least one runner transitions from the first configuration to the second configuration, and/or the at least one runner is coupled to the cell so as to be disposed radially outward of the leaflets, and/or the at least one runner has first and second ends coupled to the cell, and/or the first end of the at least one runner is coupled to a first strut of the cell and the second end of the at least one runner is coupled to a second strut of the cell, and/or the first end of the at least one runner is coupled to a junction of a first two struts of the cell and the second end of the at least one runner is coupled to a junction of a second two struts of the cell, and/or the first strut is diagonally opposed to the second strut when the stent is in the collapsed condition, and/or the at least one runner is coupled to the cell at an attachment end, the at least one runner being wider at the attachment end than at its midpoint, and/or the at least one runner includes a first runner and a second runner coupled to the cell, and/or the first runner and the second runner are coupled together at their midpoints, and/or the stent has length direction between a proximal end and a distal end, and the at least one runner extends substantially in the length direction in the second configuration, and/or the at least one runner extends substantially in a circumferential direction of the stent in the second configuration.

In some embodiments, a prosthetic heart valve for replacing a native valve includes a stent including a plurality of struts forming cells, the stent having a collapsed condition and an expanded condition. A valve assembly is disposed within the stent, the valve assembly including a plurality of leaflets and a cuff. A nested strut is coupled to a cell, the nested strut being configured to transition from a first configuration to a second configuration when the stent moves from the collapsed condition to the expanded condition, the nested strut projecting radially outwardly from the cell in the second configuration.

In some examples, a nested strut may be substantially U-shaped in the collapsed condition, and/or the nested strut extends substantially in a circumferential direction of the stent in the second configuration.

The invention claimed is:

1. A prosthetic heart valve for replacing a native valve, comprising:
   a stent including a plurality of struts forming cells, the stent having a collapsed condition and an expanded condition;
   a valve assembly disposed within the stent, the valve assembly including a plurality of leaflets and a cuff; and
   at least one runner coupled to an intersection of struts of a selected cell, the selected cell having four struts that circumscribe the at least one runner, the at least one runner being configured to transition from a first configuration to a second configuration when the stent moves from the collapsed condition to the expanded condition, the at least one runner projecting radially outwardly from a surface of the selected struts of the selected cell in the second configuration, wherein the at least one runner has a first terminal end coupled to the intersection of the struts of the selected cell, and an unattached end opposite the first terminal end.

2. The prosthetic heart valve of claim 1, wherein the selected cell is diamond-shaped.

3. The prosthetic heart valve of claim 1, wherein the at least one runner is linear in the first configuration.

4. The prosthetic heart valve of claim 1, wherein the at least one runner is bowed or curved in the second configuration.

5. The prosthetic heart valve of claim 1, wherein the at least one runner pushes the cuff radially outwardly when the at least one runner transitions from the first configuration to the second configuration.

6. The prosthetic heart valve of claim 5, wherein the at least one runner is disposed radially outward of the leaflets.

7. The prosthetic heart valve of claim 1, wherein the stent has a length direction between a proximal end of the stent and a distal end of the stent, and the at least one runner extends substantially in the length direction in the second configuration.

8. The prosthetic heart valve of claim 1, wherein each of the cells has a first strut, a second strut, a third strut and a fourth strut collectively forming a closed shape with one another.

9. The prosthetic heart valve of claim 8, wherein the first strut is directly joined to the second strut and one of the third strut and the fourth strut.

10. The prosthetic heart valve of claim 1, wherein the stent includes an aortic section having a first diameter, and an annulus section having a second diameter, the first diameter being larger than the second diameter in the expanded condition, and wherein the selected cell is in the annulus section.

11. The prosthetic heart valve of claim 1, wherein the selected cell is disposed in a proximalmost row of cells.

\* \* \* \* \*